United States Patent
Lin et al.

(10) Patent No.: US 8,216,549 B2
(45) Date of Patent: Jul. 10, 2012

(54) METHOD FOR MAKING A LIGAND-QUANTUM DOT CONJUGATE

(75) Inventors: Shu-Yi Lin, Hsinchu (TW); Leu-Wei Lo, Taipei (TW); Chung-Shi Yang, Taichung (TW)

(73) Assignee: National Health Research Institutes, Miaoli County (TW)

( * ) Notice: Subject to any disclaimer, the term of this patent is extended or adjusted under 35 U.S.C. 154(b) by 467 days.

(21) Appl. No.: 12/485,922

(22) Filed: Jun. 17, 2009

(65) Prior Publication Data

US 2010/0021957 A1    Jan. 28, 2010

Related U.S. Application Data

(60) Provisional application No. 61/083,614, filed on Jul. 25, 2008.

(51) Int. Cl.
```
A61K 49/00     (2006.01)
A61K 38/00     (2006.01)
C12Q 1/68      (2006.01)
C12N 11/00     (2006.01)
C12N 11/14     (2006.01)
C07K 17/00     (2006.01)
C07K 17/14     (2006.01)
C07H 21/00     (2006.01)
```
(52) U.S. Cl. ......... 424/9.1; 435/6.1; 435/174; 435/176; 514/1.1; 530/402; 536/22.1
(58) Field of Classification Search .................. None
See application file for complete search history.

(56) References Cited

U.S. PATENT DOCUMENTS

| | | | | |
|---|---|---|---|---|
| 4,507,466 | A * | 3/1985 | Tomalia et al. | 528/332 |
| 5,165,923 | A * | 11/1992 | Thorpe et al. | 424/179.1 |
| 5,196,478 | A * | 3/1993 | Varga et al. | 525/54.1 |
| 5,465,151 | A * | 11/1995 | Wybourne et al. | 356/481 |
| 6,221,602 | B1 * | 4/2001 | Barbera-Guillem et al. | 435/6.11 |
| 6,872,450 | B2 * | 3/2005 | Liu et al. | 428/403 |
| 7,449,299 | B2 * | 11/2008 | Bauer | 435/20 |
| 7,498,177 | B2 * | 3/2009 | De La Fuente et al. | 436/524 |
| 7,998,923 | B2 * | 8/2011 | Pinaud et al. | 514/1.1 |
| 2004/0175504 | A1 * | 9/2004 | Hasselblatt et al. | 427/354 |
| 2006/0051878 | A1 | 3/2006 | Dickson | |
| 2006/0148104 | A1 * | 7/2006 | Marini et al. | 436/524 |

OTHER PUBLICATIONS

13. Zheng, J.; Zhang, C.; Dickson, R. M. (2004) Highly fluorescent, water-soluble, size-tunable gold quantum dots. Physical Review Letters 93: 077402.

Lin. S. Y.; Chen, N. T.; Sum, S. P.; Lo, L. W., Yang, C. S. (2008) Cellular internalization of photoluminescent gold quantum dots modified with nuclear leading sequence peptides. Chem Commun 39:4762-4764.

* cited by examiner

*Primary Examiner* — David Naff
(74) *Attorney, Agent, or Firm* — Hsiu-Ming Saunders; Intellectual Property Connections, Inc.

(57) ABSTRACT

A quantum dot (QD) conjugate comprises a QD and a ligand conjugated with the QD, in which the ligand has at least one thiol and at least one other functional group. The QD conjugate may further comprise a bioactive agent covalently coupled to the ligand to form a bioactive agent-tagged QD conjugate. A method for preparing a QD conjugate comprises the steps of: (1) providing a solution comprising a QD encapsulated within a dendrimer; (2) adding into the solution a ligand; and (3) allowing an exchange between the ligand and the dendrimer for the QD to obtain a ligand-QD conjugate, in which the ligand is covalently conjugated to the surface of the QD. The method may further comprise the step of coupling the ligand-QD conjugate to a bioactive agent to obtain a bioactive agent-tagged ligand-QD conjugate.

20 Claims, 4 Drawing Sheets

SEQUENCE LISTING

```
<160> NUMBER OF SEQ ID NOS: 2

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
```

```
-continued
<211> LENGTH: 16
<212> TYPE: PRT
<213> ORGANISM: Xenopus laevis

<400> SEQUENCE: 2

Lys Arg Pro Ala Ala Thr Lys Lys Ala Gly Gln Ala Lys Lys Lys Lys
1               5                   10                  15
```

METHOD FOR MAKING A LIGAND-QUANTUM DOT CONJUGATE

REFERENCES TO RELATED APPLICATION

The present application claims priority to U.S. Provisional Application Ser. No. 61/083,614, filed Jul. 25, 2008, which is herein incorporated by reference in its entirety.

FIELD OF THE INVENTION

The present invention relates generally to quantum dots, and more specifically to functionalized quantum dots.

BACKGROUND OF THE INVENTION

Gold nanoclusters such as nanosphere and nanorod are of great potential in biological applications due to their small sizes, excellent biocompatibility and unique optical properties, including the well-characeterized surface plasmon resonance (SPR) phenomenon [1-6]. Gold nanoclusters have size-dependent SPR absorption in visible wavelength range; decreasing their sizes into less than 3 nm will induce the disappearance of the SPR and the emergence of photoluminescence [7-10]. The photoluminescence quantum yields of gold nanoclusters can be enhanced several orders of magnitude if their sizes are further decreased into the sub-nm scale [11-13]. This type of novel nanoclusters, termed as gold quantum dots (GQDs), have remarkable small size and excellent photoluminescent efficiency, which may be valuable properties toward their applicability in chemistry and biology [14,15].

To prepare GQDs with high quantum yield, it is essential to manipulate the nucleation of gold within a well-defined molecular scaffold. For example, thiolate-protected GQDs can be prepared by chemical reduction of the complex formed, from gold ions with alkanthiols, but the quantum yield is reduced because of their size-polydispersion since the gold core significant growth is influenced by the number of thiols [16-18]. Recently, polyamidoamine (PAMAM) dendrimer-encapsulated gold ions have been used to prepare GQDs with mono-dispersed size and excellent quantum efficiency [11-13]. Although the dendrimers are excellent molecular templates for the GQD formation, their safety still remain to be clarified prior to biological applications since there has been reported that they may have cytotoxcity such as inducing haemolysis of human red blood cells [19,20].

A heretofore unaddressed need exists in the art to address the deficiencies and inadequacies, especially in connection with dendrimer-encapsulated quantum dots.

SUMMARY OF THE INVENTION

In one aspect, the invention relates to a quantum dot (QD) conjugate. The QD conjugate comprises a QD and a ligand conjugated with the QD, in which the ligand is not a repeatedly branched dendrimer and has at least one thiol and at least one other functional group. The QD conjugate may further comprise a bioactive agent covalently coupled to the ligand to form a bioactive agent-tagged QD conjugate. The bioactive agent is covalently coupled to the ligand via a cross-linker.

In one embodiment of the invention, the QD comprises gold, silver, platinum or palladium.

In another embodiment of the invention, the ligand has at least one other functional group that is selected from the group consisting of carboxyl, hydroxyl, aldehyde and primary amine.

In another embodiment of the invention, the ligand has at least one other functional group that is carboxyl. For example, the ligand may be a carboxylate-terminated n-alkanethiol such as 11-mercaptoundecanonic acid (MUDA).

In another aspect, the invention relates to a QD conjugate consisting essentially of a QD and a ligand conjugated to the QD, in which the ligand is not a repeatedly branched dendrimer and has at least one thiol and at least one other functional group.

In another aspect, the invention relates to a QD conjugate consisting essentially of a QD, a ligand conjugated to the QD and a bioactive agent coupled to the ligand to form a bioactive agent-tagged QD conjugate, in which the ligand is not a repeatedly branched dendrimer and has at least one thiol and at least one other functional group.

Further In another aspect, the invention relates to a QD conjugate consisting of a QD and a ligand conjugated with the QD, in which the ligand is not a repeatedly branched dendrimer and has at least one thiol and at least one other functional group.

In another aspect, the invention relates to a QD conjugate consisting of a QD, a ligand conjugated to the QD and a bioactive agent coupled to the ligand to form a bioactive agent-tagged QD conjugate, in which the ligand is not a repeatedly branched dendrimer and has at least one thiol and at least one other functional group.

In another aspect, the invention relates to a method for making a QD conjugate comprising the following steps: (a) providing a solution comprising a quantum dots (QD) encapsulated within a dendrimer; (b) adding into the solution a ligand having at least one thiol and at least one other functional group; and (c) replacing the dendrimer with the ligand to obtain a ligand-QD conjugate, wherein the ligand is covalently conjugated to the surface of the QD.

In one embodiment of the invention, the method further comprises coupling the ligand-QD conjugate to a bioactive agent to obtain a bioactive agent-tagged ligand-QD conjugate. The bioactive agent may be selected from the group consisting of a protein, a peptide, a nucleic acid and a carbohydrate. The protein or peptide may comprise an amino acid sequence having a nuclear localization signal (NLS). The NLS may be derived from SV40 T antigen or nucleoplasmin.

In one embodiment of the invention, the coupling step is performed by using a cross-linking agent. The cross-linking agent may include, but not limited to, 1-[(3-dimethylamino)-propyl]-3-ethylcarbodiimide hydrochloride (EDC).

Further in another aspect, the invention relates to a QD conjugate prepared by the aforementioned method. The QD conjugate as prepared comprises a QD and a ligand conjugated to the QD, wherein the ligand has at least one thiol and at least one other functional group. The QD conjugate as prepared may further comprise a bioactive agent covalently coupled to the ligand.

Further in another aspect, the invention relates to a method for performing intracellular imaging on a cell. The method comprises exposing a cell to the aforementioned QD conjugate and obtaining a fluorescent image of the cell.

Yet in another aspect, the invention relates to a method for labeling a biological target with a QD conjugate. The method comprises exposing the biological target to the aforementioned bioactive agent-tagged QD conjugate, wherein the bioactive agent is specific to the biological target; and allowing the target and the bioactive agent of the QD conjugate to interact and thereby labeling the biological target with the bioactive agent-tagged ligand-QD conjugate. The biological target may be a receptor or an antigen.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
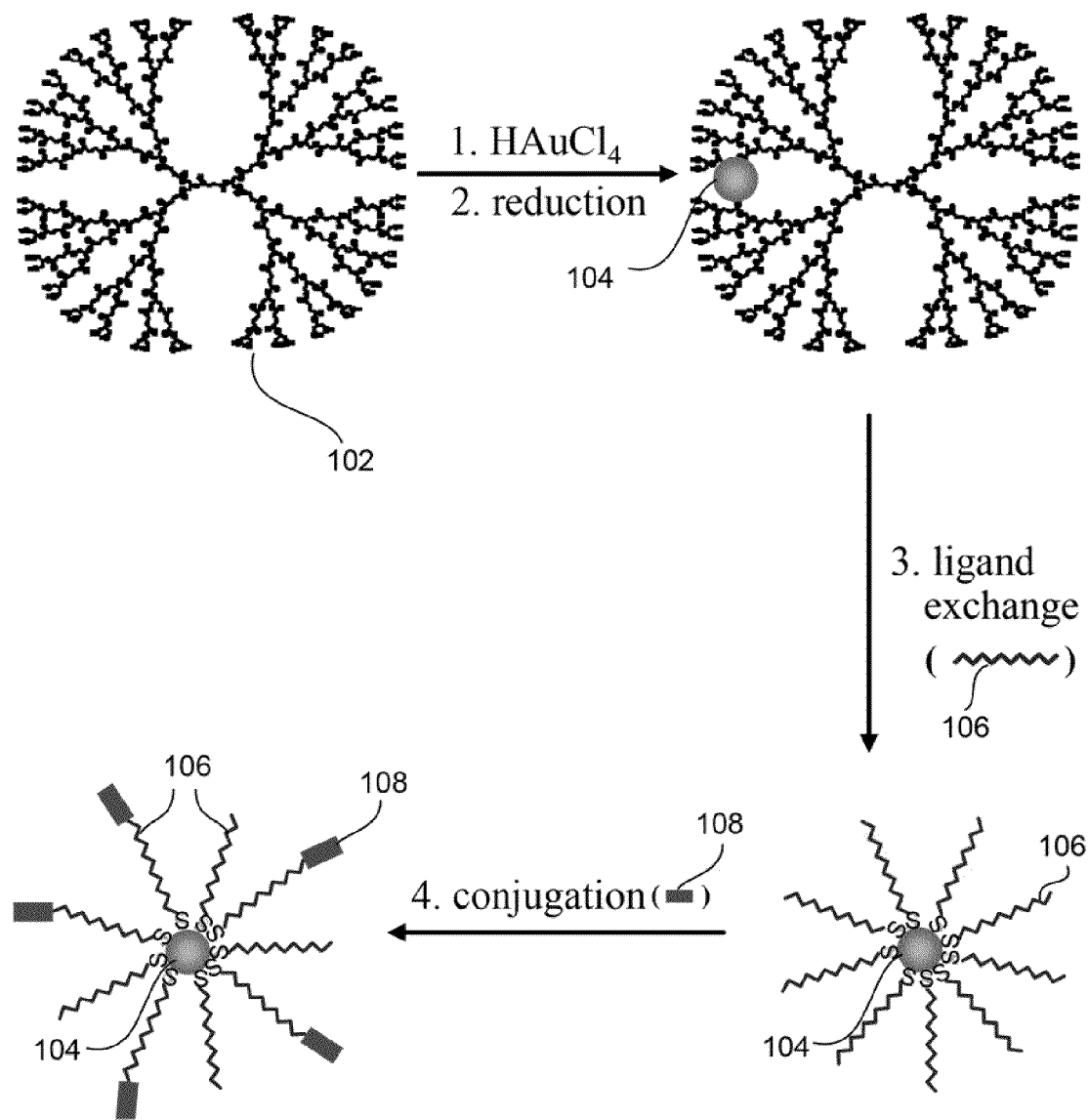
FIG. 1 is a schematic drawing showing a proposed strategy for GQD synthesis, ligand exchange and derivatization.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within. 10 percent, and more preferably within 5 percent of a given value or range. Numerical quantities given herein are approximate, meaning that the term "around", "about" or "approximately" can be inferred if not expressly stated.

As used herein, "dendrimers" are regular, highly branched monomers leading to a monodisperse, tree-like or generational structure.

As used herein, the term "ligand" is a molecule or a molecular group that binds to another chemical entity to form a larger complex.

As used herein, "a nuclear localization signal or sequence (NLS)" is an amino acid sequence which acts like a "tag" on the exposed surface of a protein. This sequence is used to target the protein to the cell nucleus through the Nuclear Pore Complex and to direct a newly synthesized protein into the nucleus via its recognition by cytosolic nuclear transport receptors. Typically, this signal consists of one or more short sequences of positively charged lysines or arginines. For example, the NLS of SV40 large T antigen is PKKKRKV (SEQ ID NO: 1) and the NLS of nucleoplasmin is KR[PAAT-KKAGQA]KKKK (SEQ ID NO: 2).

The full names for abbreviations used herein are as follows: PAMAM for polyamidoamine, MUDA for 11-mercaptoundecanonic acid, HRTEM for High-resolution transmission electron microscopy (HRTEM), EDC for 1-[(3-dimethylamino)-propyl]-3-ethylcarbodiimide hydrochloride.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit, the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

Preparation of GQDs Capped with 11-Mecaptodecanonic Acid (MUDA) via Ligand Exchange. All chemicals were purchased from Aldrich except they are indicated otherwise. To synthesize GQDs in sub-nm diameter, the gold ions (0.2 wt % in aqua, 1.5 μmol) were added into 5 mL of water (18 MΩ $cm^{-1}$) containing hydroxyl-terminated polyamidoamine (PAMAM, 10 wt % in methanol, 0.25 μmol). For example, 290 μL of 0.2 weight % of gold ions $HAuCl_4$ were mixed with 40 μl of 10 weight % of PAMAM dissolved in water.

The solution was stirred at a frequency of about 40 times per minute in a cold room (4° C.) for 24 h until color changed from pale yellow to blue and then shaken at 37° C. for 3 days. Ligand exchange of GQDs was performed by adding MUDA (20 mM in ethanol 20 μL or 100 μl) into PAMAM-encapsulated GQD aqua. The mixture was stirred in a dark room for 2 days. PAMAM were excluded from GQD aqua by dialysis using a 3 KDa molecular weight cut-off membrane, which further removed excess MUDA. For dialysis, the dialysis membrane was loaded with the sample and stirred in water for about 48 hours. The MUDA-GQDs were lyophilized and stored in dark.

Cellular Uptake. HeLa cells were cultured at a cell density of about 1×10⁵ cells per plate in a humidified atmosphere with 5% $CO_2$. The cell culture medium contained Minimum Essential Medium (MEM; Gibco) supplemented with 10% fetal bovine serum (FBS; Hyclone). For imaging by confocal microscopy, cells were plated 24 hrs before experiments. After incubation with GQD or GQD-SV40 (0.6 mM) for 1.5 hrs, cells were stained with membrane-specific dye, wheat germ agglutinin (WGA) 594 and with nuclear-specific dye, SYTO 59. (Cell images were captured by a Leica TCS confocal spectral microscope using 63× oil immersion objective. The two dyes, WGA 594 and SYTO 59, were purchased from Invitrogen. The GQDs emitted blue fluorescence by exciting with a laser light at 405 nm.

Results

The invention relates to a novel strategy utilizing 11-mercaptoundecanonic acid (MUDA) 106 as a ligand to exchange GQDs 104 (MUDA-GQDs) from PAMAM 102 encapsulation before surface functionalization (FIG. 1). MUDA 106 is a negatively charged thiol that exhibits strong interactions with gold and has been reported to be of much less safety concerns [21]. MUDA 106 is not only a protector to maintain the GQDs 104 stability in water, but also a building block to conjugate the GQDs 104 with various biomolecules 108 such as a specific peptide named SV40 nuclear localization signal (NLS) 108, which was used in the current study. Anchoring of such peptides 108 on the sub-nm sized GQDs 104 can facilitate their transport into the nucleus, assessable with the bright photoluminescence of the GQDs. The strategic synthesis and functionalization of the GQDs based on ligand exchange will become a prerequisite and accessible method for extending their applications into various interestingly topics.

Figure 2:
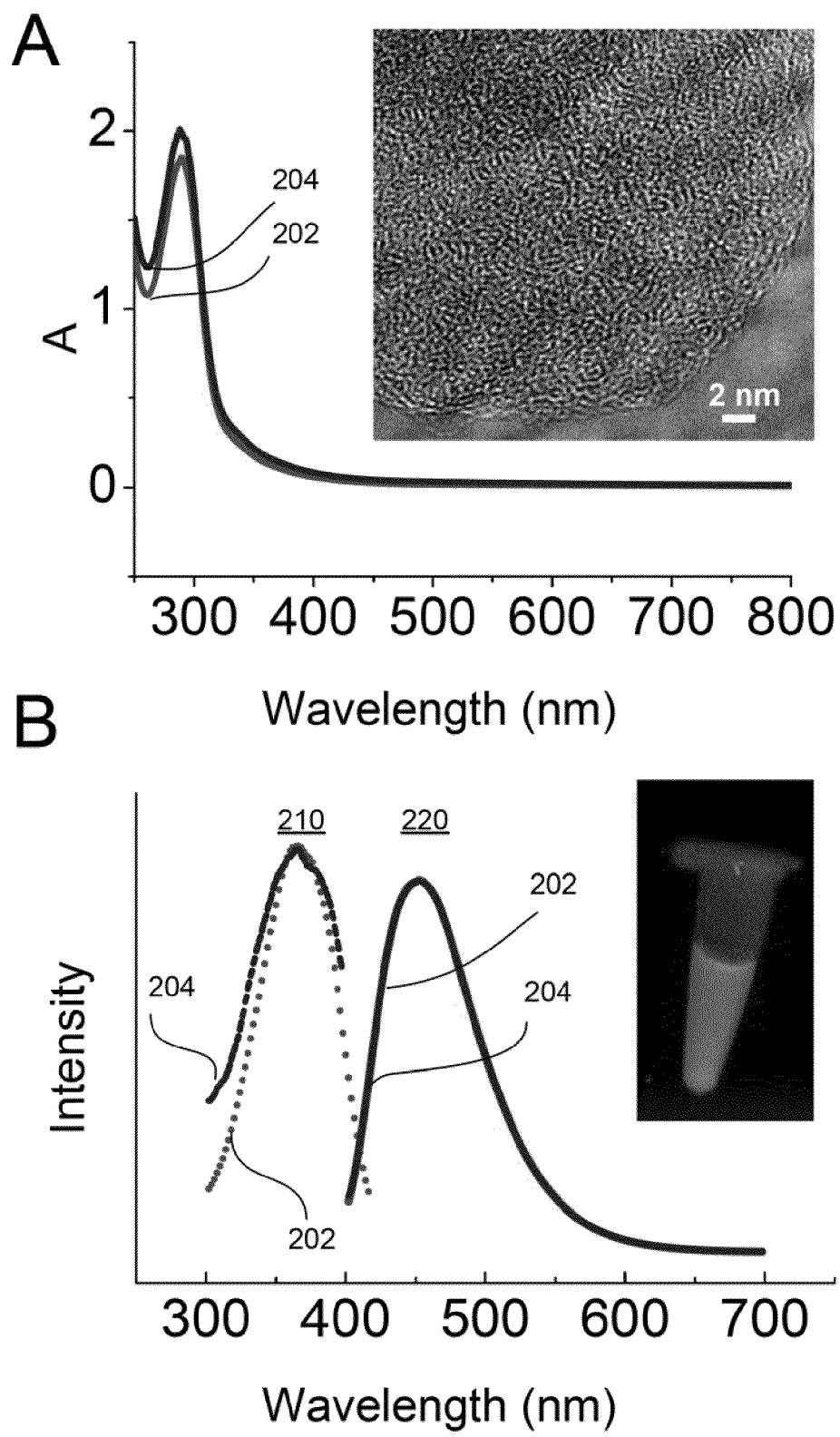
FIG. 2A shows the absorption spectra of GQDs 202 and MUDA-GQDs 204. The inset is an HRTEM image of MUDA-GQDs. The average core size of the GQD is less than 1 nm.
FIG. 2B shows the photoluminescent spectra of the GQDs 202 and MUDA-GQD 204 in FIG. 1A under excitation 210 and emission 210. The inset is a photo showing photoluminescence emission from MUDA-GQDs under UV lamp irradiation (366 nm).

In this study, the fourth-generation of hydroxyl-terminated PAMAM dendrimer ($G_4OH$) containing blue-light emitting GQDs was synthesized at physiological temperature (37° C.) according to previous method [12]. The 3 μmol gold ions ($HAuCl_4$, 0.2 wt % water solution) were added to 5 mL of deionized water containing 0.25 μmol $G_4OH$ (10 wt % methanol solution). The solution was incubated in cold room (4° C.) for 24 h until the gold ions were sequestered into $G_4OH$. Then the mixture was kept at 37° C. for 3 days to produce dendrimer-encapsulated GQDs. FIG. 2A is the absorption sepctrum of the GQDs, which shows no SPR band at 520 nm (line 202), indicating that the sizes of GQDs are smaller than 1 nm. After introducing MUDA onto the GQDs, similar absorption spectrum was observed (FIG. 2A, line 204), suggesting that the GQD size did not alter before and after the exchange. The GQDs exhibited photoluminescence with excitation 210 and emission 220 peaks at 370 nm and 450 nm (FIG. 2B, line 202), respectively, which correspond to the published values [12]. Ligand exchange with MUDA did not appear to alter GQD's photoluminescence exciaiton and eminssion wavelengths (FIG. 2B, line 204). These results suggest that the photoluminescent properties of the GQDs are unaffectd by the ligand exchange [23].

Figure 3:
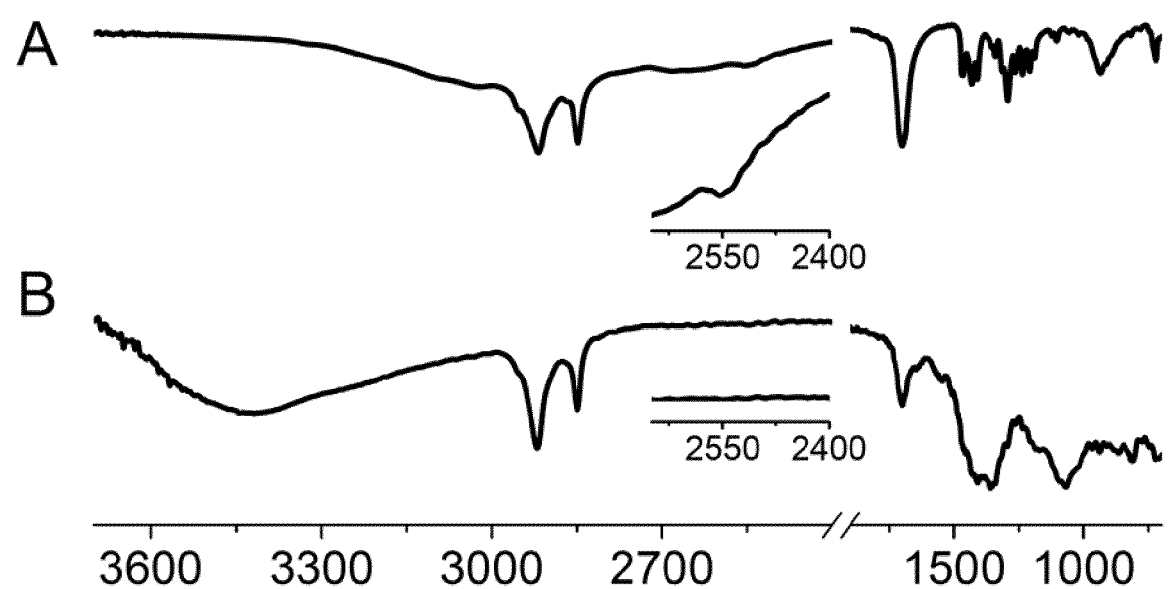
FIG. 3A shows the transmission FTIR spectra of MUDA. The wavelengths for the magnified sections range from 2400 to 2650 $cm^{-1}$.
FIG. 3B shows the transmission FTIR spectra of MUDA-GQDs in a KBr pellet. The wavelengths for the magnified sections range from 2400 to 2650 $cm^{-1}$.

MUDA-GQDs were purified by dialysis and dried by lyophilizer before transmission IR measurements. FIGS. 3A and 3B show typical transmission IR spectra of MUDA alone and MUDA-GQDs, respectively. There are three significant differences in FIG. 3B as compared to 3A. First, as shown in the inset of the enlarged section between 2400 and 2650 $cm^{-1}$, the S-H stretch band around 2550 $cm^{-1}$ is absent, resulting from the formation of the gold-sulfur bond. Second, the absorption 3400 $cm^{-1}$ is a result of residual moisture within the dried GQDs. Third, the peaks at 2919, 2850, 1700, 1560, 1410 and 1077 $cm^{-1}$ are vibrational modes of $U_{asy}(CH_2)$, $U_{sym}(CH_2)$, $U_{str}(C=O)$, $U_{asy}(CO_2^-)$, $U_{sym}(CO_2^-)$ and $U_{str}(CO)$, respectively. These vibrational bands confirm the association of MUDA with GQDs.

Figure 4:
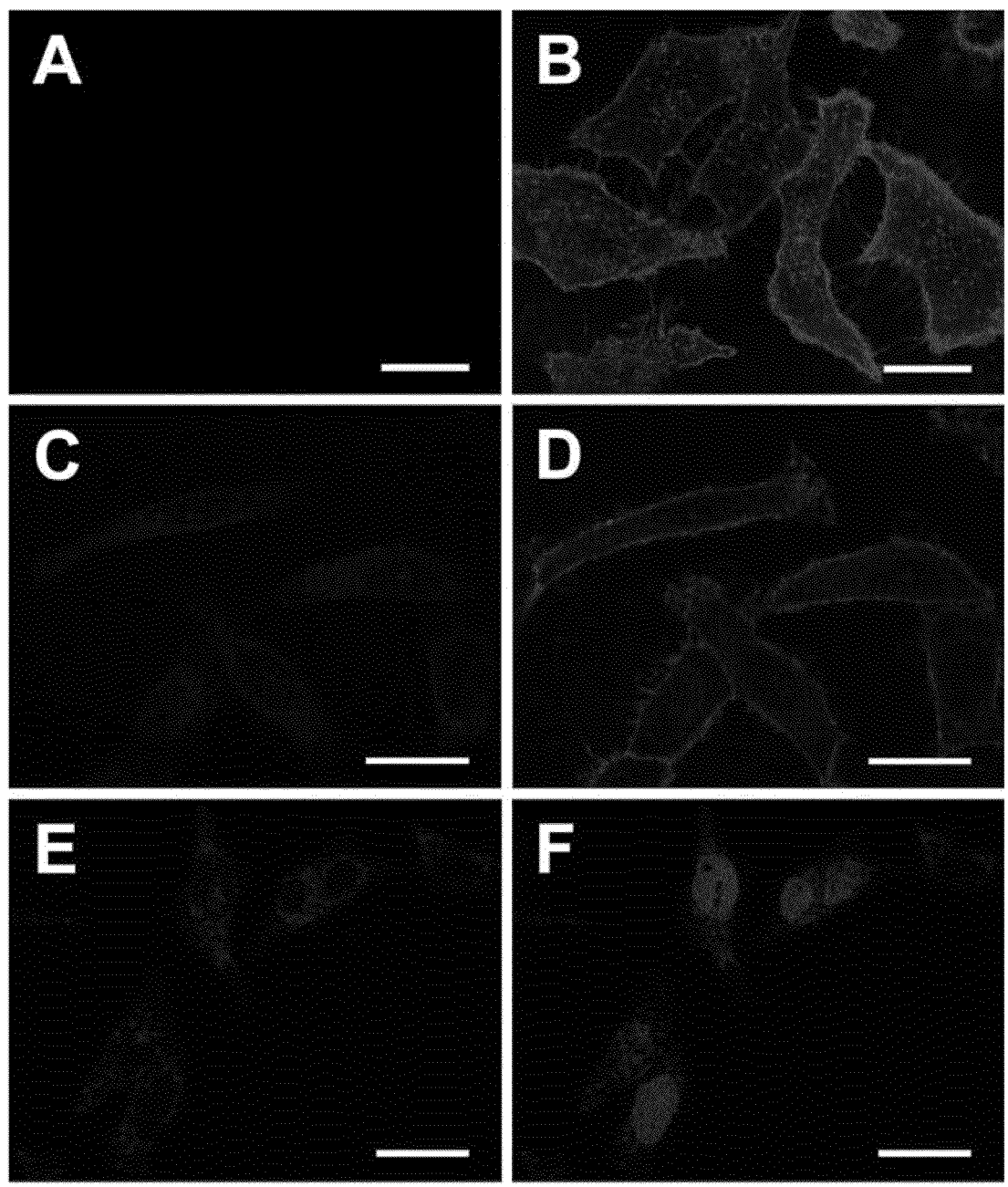
FIGS. 4A-4B are confocal microscope images of MUDA-GQDs-treated HeLa cells. Scale bar: 25 μm.
FIGS. 4C-4F are confocal microscope images of NLS-MUDA-GQDs-treated HeLa cells. Scale bar: 25 μm.

To modify MUDA-GQDs surface with NLS (NLS-MUDA-GQDs) for nuclear transport, 1-[3-dimethylamino)-propyl]-3-ethylcarbodiimide hydrochloride (EDC) was then introduced to activate the carboxylic acid of MUDA before adding NLS. FIG. 4 show photoluminescence images from the MUDA-GQDs (without NLS) and NLS-MUDA-GQDs measured by the cofocal microscope, respectively. The one-color image shows no photoluminescent signal (panel A) from the cells treated with MUDA-GQDs, implicating MUDA-GQDs were not able to enter the cells efficiently due to, at least in part, the negative surface-charge. On the contrary, intensive blue photoluminescence (panel C and E) from NLS-MUDA-GQDs were observed, indicative of the internalization of the MUDA-GQDs associated with NLS by HeLa cells. To illustrate the intracellular and nuclear distribution of NLS-MUDA-GQDs, the cells were counter-stained with a specific membrane dye, wheat germ agglutinin conjugated Alexa 594 (WGA-Alexa 594), and a nuclear dye, SYTO 59. The images of two-color colocalization (panel D and F) revealed that the blue photoluminescent signals from NLS-MUDA-GQDs are well-distributed within both the cytoplasm (panel D) and the nucleus (panel F), in comparison with the image of cells treated with MUDA-GQDs (panel B) where only red fluorescence signals of WGA-Alexa 594 were observed. Therefore, the nuclear targeting of MUDA-GQDs are able to be achieved by the functionality of NLS, as shown in panel F with the two-color colocalization of images at the same confocal z-plane (blue; NLS-MUDA-GQDs; red; SYTO 59).

To summarize, the invention relates to the discovery that GQDs can be exchanged by carboxylate-terminated n-alkanethiols such as MUDA from the dendrimer-teraplate and further functionalized with site-specific leading peptides such as SV40 NLS. Additionally, the invention relates to the discovery that GQDs may be applied as promising optical beacons for intracellular imaging and agents for subcellular targeting.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

References

1. Shi, X.; Wang, S.; Meshinchi, S.; Antwerp, M. E. V.; Bi, X.; Lee, I.; Baker Jr., J. R. "Dendrimer-Entrapped Gold Nanoparticles as a Platform for Cancer-Cell Targeting and Imaging" small (2007) 3: 1245.
2. Oyelere, A. K.; Chen, P. C; Huang, X,; El-Sayed, I. H.; El-Sayed, M. A. "Peptide-Conjugated Gold Nanorods for Nuclear Targeting" Bioconjugate Chemistry (2007) 18: 1490
3. Dahl, J. A.; Maddux, B. L.; Hutchison, J. E. "Toward greener nanosynthesis" Chemical Reviews (2007) 107: 2228.
4. Eustis, S.; El-Sayed, M. A. "Why gold nanoparticles are more precious than pretty gold: noble metal surface plasmon resonance and its enhancement of the radiative and nonradiative properties of nanocrystals of different shapes" Chemical Society Reviews (2006) 35: 209.
5. Chen, C.-C.; Lin, Y.-P.; Wang, C.-W.; Tzeng, H.-C.; Wu, C.-H.; Chen, Y.-C.; Chen, C.-P.; Chen, L.-C.; Wu, Y.-C. "DNA-Gold Nanorod Conjugates for Remote Control of Localized Gene Expression by near Infrared Irradiation" Journal of the American Chemical Society (2006) 128: 3709.
6. Connor, E. E.; Mwamuka, J.; Anand Gole; Murphy, C. J.; Wyatt, M. D. "Gold Nanoparticles Are Taken Up by Human Cells but Do Not Cause Acute Cytotoxicity" small (2005) 1: 325.
7. Sham, T. K.; Kim, P.-S. G.; Zhang, P. "Electronic structure of molecular-capped gold nanoparticles from X-ray spectroscopy studies: Implications for coulomb blockade, luminescence and non-Fermi behavior" Solid State Communications (2006) 138: 553
8. Sham, T. K.; Kim, P.-S. G.; Zhang, P. "Electronic structure of molecular-capped gold nanoparticles from X-ray spectroscopy studies: Implications for coulomb blockade, luminescence and non-Fermi behavior" Solid State Communications (2006) 138: 553.
9. Huang, T.; Murray, R. W. "Visible Luminescence of Water-Soluble Monolayer-Protected Gold Clusters" Journal of Physical Chemistry B (2001) 105: 12498.
10. Templeton, A. C; Chen, S.; Gross, S. M.; Murray, R. W. "Water-Soluble, Isolable Gold Clusters Protected by Tiopronin and Coenzyme A Monolayers" Langmuir (1999) 15: 66.
11. Zheng, J.; Nicovieh, P. R.; Dickson, R. M. "Highly fluorescent noble-metal quantum dots" Annual Review of Physical Chemistry (2007) 58: 409.
12. Bao, Y.; Zhong, C.; Vu, D. M.; Temirov, J. P.: Dyer, R. B.: Martinez, J. S. "Nanoparticle-free synthesis of fluorescent gold nanoclusters at physiological temperature" Journal of Physical Chemistry C (2007) 111: 12194.
13. Zheng, J.; Zhang, C.; Dickson, R. M. "Highly fluorescent, water-soluble, size-tunable gold quantum dots" Physical Review Letters (2004) 93: 077402.
14. Huang, C. C.; Yang, Z.; Lee, K. H.; Chang, H. T. "Synthesis of highly fluorescent gold nanoparticles for sensing mercury(II)" Angewandte Chemie, International Edition in English (2007) 46: 6824.
15. Triulzi, R. C.; Micic, M.; Giordani, S.; Serry, M.; Chioue, W.-A.; Leblanc, R. M. "Immunoassay based on the antibody-conjugated PAMAM-dendrimer-gold quantum dot complex" Chemical Communications (2006) 5068.
16. Negishi, Y.; Nobusada, K.; Tsuknda, T. "Glutathione-Protected Gold Clusters Revisited: Bridging the Gap between Gold(I)-Thiolate Complexes and Thiolate-Protected Gold Nanocrystals" Journal of the American Chemical Society (2005) 127: 5261
17. Wilcoxon, J. P.; Martin, J. E. "Photoluminescence from nanosize gold clusters" Journal of Chemical Physics (1998) 108: 9137
18. Schaaff, T. G.; Knight, G.; Shafigullin, M. N.; Borkman, R. F.; Whetten, R. L. "Isolation and Selected Properties of a 10.4 kDa Gold:Glutathione Cluster Compound" Journal of Physical Chemistry B (1998) 102: 10643.
19. Duncan, R.; Izzo, L. "Dendrimer biocompatibility and toxicity" Advanced Drug Delivery Reviews (2005) 57: 2215.
20. Doman'ski, D. M.; Klajnert, B.; Bryszewska, M. "Influence of PAMAM dendrimers on human red blood cells" Bioelectrochemistry (2004) 63: 189.
21. Ren, L.; Huang, X. L.; Zhang, B.; Sun, L. P.; Zhang, Q. Q.; Tan, M. C.; Chow, G. M. "Cisplatin-loaded Au—Au2S nanoparticles for potential cancer therapy: cytotoxicity, in vitro carcinogenicity, and cellular uptake" Journal of Biomedical Materials Research, Part A (2008) 85: 787.
22. Dingwall C. et al. (1988) "The nucleoplasmin nuclear location sequence is larger and more complex than that of SV-40 large T antigen" *The Journal of Cell Biology* 107: 841-849.
23. Lin, S. Y.; Chen, N. T.: Sum, S. P.; Lo, L. W.; Yang, C. S. (2008) Cellular internalization of photoluminescent gold quantum dots modified with nuclear leading sequence peptides. Chem Commun 39:4762-4764.

---

What is claimed is:

1. A method for making a quantum dot conjugate comprising:
   a) providing a solution comprising a quantum dot (QD) encapsulated within a dendrimer;
   b) adding into the solution a ligand having at least one thiol and at least one other functional group; and
   c) replacing the dendrimer with the ligand to obtain a ligand-QD conjugate, wherein the ligand is covalently conjugated to the surface of the QD.

2. The method of claim 1, further comprising the step of:
   d) coupling the ligand-QD conjugate to a bioactive agent to obtain a bioactive agent-tagged ligand-QD conjugate.

3. The method of claim 2, wherein the coupling step is performed in the presence of a cross-linking agent.

4. The method of claim 1, wherein the at least one other functional group is selected from the group consisting of carboxyl, hydroxyl, aldehyde and primary amine.

5. The method of claim 2, wherein the bioactive agent is selected from the group consisting of a protein, a peptide, a nucleic acid and a carbohydrate.

6. The method of claim 5, wherein the protein or peptide comprises an amino acid sequence having a nuclear localization signal (NLS).

7. The method of claim 1, wherein the QD comprises gold, silver, platinum or palladium.

8. The method of claim 1, wherein the QD comprises gold.

9. The method of claim 1, wherein the at least one other functional group is carboxyl.

10. The method of claim 1, wherein the dendrimer comprises a hydroxyl-terminated polyamidoamine (PAMAM) dendrimer.

11. The method of claim 1, wherein the ligand comprises 11-mercaptoundecanoic acid and the dendrimer comprises a hydroxyl-terminated PAMAM dendrimer.

12. The method of claim 1, wherein the ligand comprises carboxylate-terminated n-alkanethiols.

13. The method of claim 12, wherein the ligand comprises 11-mercaptoundecanonic acid.

14. The method of claim 2, wherein the ligand comprises carboxylate-terminated n-alkanethiols.

15. The method of claim 14, wherein the ligand comprises 11-mercaptoundecanonic acid.

16. The method of claim 2, further comprising:
   e) exposing a biological target to the bioactive agent-tagged ligand-QD conjugate, wherein the bioactive agent is specific to the target; and
   f) allowing the target and the bioactive agent of the ligand-QD conjugate to interact and form a biological target-labeled bioactive agent-tagged ligand-QD conjugate.

17. The method of claim 16, wherein the biological target is a receptor or an antigen.

18. The method of claim 16, wherein the bioactive agent is selected from the group consisting of a protein, a peptide, a nucleic acid and a carbohydrate.

19. A QD conjugate prepared by the method of claim 1, comprising:
   a) a QD; and
   b) a ligand conjugated with the QD, wherein the ligand has at least one thiol and at least one other functional group.

20. A QD conjugate prepared by the method of claim 2, comprising:
   a) a QD;
   b) a ligand conjugated with the QD, wherein the ligand has at least one thiol and at least one other functional group; and
   c) a bioactive agent covalently coupled to the ligand, wherein the bioactive agent is covalently coupled to the ligand via a cross-linker.

* * * * *